United States Patent
Sturtevant et al.

(10) Patent No.: US 10,913,888 B2
(45) Date of Patent: *Feb. 9, 2021

(54) NANOTUBE MEDIATION OF DEGRADATIVE CHEMICALS FOR OIL-FIELD APPLICATION

(71) Applicant: MOLECULAR REBAR DESIGN, LLC, Austin, TX (US)

(72) Inventors: Bryce Daniel Sturtevant, Austin, TX (US); August Charles Krupp, Austin, TX (US)

(73) Assignee: Molecular Rebar Design, LLC, Austin, TX (US)

( * ) Notice: Subject to any disclaimer, the term of this patent is extended or adjusted under 35 U.S.C. 154(b) by 154 days.

This patent is subject to a terminal disclaimer.

(21) Appl. No.: 16/092,141

(22) PCT Filed: Apr. 7, 2017

(86) PCT No.: PCT/US2017/026673
§ 371 (c)(1),
(2) Date: Oct. 8, 2018

(87) PCT Pub. No.: WO2017/177176
PCT Pub. Date: Oct. 12, 2017

(65) Prior Publication Data
US 2019/0127628 A1    May 2, 2019

Related U.S. Application Data

(60) Provisional application No. 62/424,606, filed on Nov. 21, 2016, provisional application No. 62/319,599, filed on Apr. 7, 2016.

(51) Int. Cl.
| | |
|---|---|
| *C09K 8/66* | (2006.01) |
| *C09K 8/70* | (2006.01) |
| *C09K 8/88* | (2006.01) |
| *C09K 8/90* | (2006.01) |
| *C09K 8/92* | (2006.01) |
| *C09K 8/68* | (2006.01) |
| *C09K 8/84* | (2006.01) |
| *B82Y 30/00* | (2011.01) |
| *B82Y 40/00* | (2011.01) |

(52) U.S. Cl.
CPC .............. *C09K 8/665* (2013.01); *C09K 8/685* (2013.01); *C09K 8/70* (2013.01); *C09K 8/706* (2013.01); *C09K 8/845* (2013.01); *C09K 8/882* (2013.01); *C09K 8/887* (2013.01); *C09K 8/90* (2013.01); *C09K 8/92* (2013.01); *B82Y 30/00* (2013.01); *B82Y 40/00* (2013.01); *C09K 2208/10* (2013.01); *C09K 2208/24* (2013.01); *C09K 2208/26* (2013.01)

(58) Field of Classification Search
CPC ............ C09K 2208/10; C09K 2208/24; C09K 2208/26; C09K 8/665; C09K 8/685; C09K 8/70; C09K 8/706; C09K 8/845; C09K 8/882; C09K 8/887; C09K 8/90; C09K 8/92; A61P 25/28; B82Y 30/00; B82Y 40/00; C01B 32/158; C01B 32/174
See application file for complete search history.

(56) References Cited

U.S. PATENT DOCUMENTS

| | | | |
|---|---|---|---|
| 2008/0194736 A1* | 8/2008 | Lu | ............................ C08J 5/005 524/35 |
| 2012/0181033 A1 | 7/2012 | Saini et al. | |
| 2014/0275286 A1* | 9/2014 | Bosnyak | ............... C01B 32/158 514/769 |
| 2015/0238476 A1 | 8/2015 | Bosnyak et al. | |
| 2017/0015895 A1 | 1/2017 | Cox et al. | |

FOREIGN PATENT DOCUMENTS

WO    2015127332 A1    8/2015

OTHER PUBLICATIONS

Yong Zhao et al., "Enzymatic Degradation of Multiwalled Carbon Nanotubes", 115 (34) J. Physical Chem. (Sep. 1, 2011), pp. 9536-9544.
Supplemental European Search Report (EP 17779935), dated Nov. 22, 2019.
Barati et al., "Polyelectrolyte Complex Nanoparticles for Protection and Delayed Release of Enzymes in Alkaline pH and at Elevated Temperature During Hydraulic Fracturing of Oil Wells", J. Appl. Polym. Sci., Authors Accepted Manuscript (2012).

* cited by examiner

*Primary Examiner* — Frances Tischler
(74) *Attorney, Agent, or Firm* — Stephen P. Krupp

(57) ABSTRACT

Discrete, individualized carbon nanotubes having targeted, or selective, oxidation levels and/or content on the interior and exterior of the tube walls can be used for nanotube-mediated controlled delivery of degradative molecules, such as oxidizers and enzymes, for oil-field drilling applications. A manufacturing process using minimal acid oxidation for carbon nanotubes may also be used which provides higher levels of oxidation compared to other known manufacturing processes.

8 Claims, No Drawings

NANOTUBE MEDIATION OF DEGRADATIVE CHEMICALS FOR OIL-FIELD APPLICATION

CROSS REFERENCE TO RELATED APPLICATIONS

The present application claims priority from U.S. application Ser. No. (U.S. Ser. No.) 62/319,599 filed on Apr. 7, 2016 and U.S. Ser. No. 62/424,606 filed Nov. 21, 2016, the entire disclosures of which are incorporated herein by reference. This application is also related to U.S. Ser. No. 14/628,248 filed Feb. 21, 2015, as well as U.S. Ser. No. 13/164,456, filed Jun. 20, 2011, and their progeny; and U.S. Ser. No. 13/140,029, filed Aug. 9, 2011 and its progeny, the entire disclosures of which are incorporated herein by reference.

FIELD OF INVENTION

The present application is directed to novel discrete carbon nanotube compositions that permit nanotube-mediated controlled delivery of degradative, viscosity reducing, molecules, such as enzymes and oxidizers, such as for oil field applications. The present application also encompasses the preparation of such carbon nanotubes with minimal acid oxidation.

BACKGROUND AND SUMMARY OF THE INVENTION

Carbon nanotubes can be classified by the number of walls in the tube, single-wall, double wall and multiwall. Carbon nanotubes are currently manufactured as agglomerated nanotube balls, bundles or forests attached to substrates. Use of carbon nanotubes as a reinforcing agent in elastomeric, thermoplastic or thermoset polymer composites is an area in which carbon nanotubes are predicted to have significant utility. However, utilization of carbon nanotubes in these applications has been hampered due to the general inability to reliably produce individualized carbon nanotubes and the ability to disperse the individualized carbon nanotubes in a polymer matrix. Bosnyak et al., in various patent applications (e.g., US 2012-0183770 A1 and US 2011-0294013 A1), have made discrete carbon nanotubes through judicious and substantially simultaneous use of oxidation and shear forces, thereby oxidizing both the inner and outer surface of the nanotubes, typically to approximately the same oxidation level on the inner and outer surfaces, resulting in individual or discrete tubes.

The present invention can utilize the tubes of those earlier Bosnyak et al. applications and disclosures, but also uses new targeted oxidation discrete tubes. The present invention describes a composition of discrete, individualized carbon nanotubes having targeted, or selective, oxidation levels and/or oxygen content on the exterior and/or interior of the tube walls. Such novel carbon nanotubes can have little to no inner tube surface oxidation, or differing amounts and/or types of oxidation between the tubes' inner and outer surfaces. These discrete tubes are useful in many applications, including plasticizers, which can then be used as an additive in compounding and formulation of elastomeric, thermoplastic and thermoset composites for improvement of mechanical, electrical and thermal properties. In particular, the present application discloses a novel manufacturing process for carbon nanotubes with minimal acid oxidation.

The present application also discloses a novel use for the carbon nanotubes in nanotube-mediated controlled delivery of degradative chemicals known in the industry as 'breakers', such as enzymes and oxidizers, for oil-field applications. Hydraulic fracturing for stimulating production from a hydrocarbon reservoir is accomplished by injecting a hydraulic fracturing fluid into the well and imposing sufficient pressure on the fracture fluid to cause formation breakdown with the attendant production of one or more fractures. The fracture or fractures may be horizontal or vertical, with the later usually predominating, and with the tendency toward vertical fracture orientation increasing with the depth of the formation being fractured. Usually a gel, an emulsion, or a foam, with normal concentrations ranging from 0.12 wt % to 0.96 wt % relative to the total weight of the fracturing fluid (see, e.g., Barati, R. et al. *A Review of Fracturing Fluid Systems Used for Hydraulic Fracturing of Oil and Gas Wells*. J. Appl. Polym. Sci. Vol. 131, 40375 (2014)), and having a proppant, such as sand or other particulate materials suspended therein, is introduced into the fracture. The proppant can include the discrete carbon nanotubes and compositions described herein. The proppant is deposited in the fracture and functions to hold the fracture open after the pressure is released and fracturing fluid is withdrawn back into the well. The fracturing fluid has a sufficiently high viscosity to penetrate into the formation to realize fracturing and to retain the proppant in suspension or at least to reduce the tendency of the proppant of settling out of the fracturing fluid. Generally, a gelation agent and/or an emulsifier is used to gel or emulsify the fracturing fluid to provide the high viscosity needed to realize the maximum benefits from the fracturing process.

After the high viscosity fracturing fluid has been pumped into the formation, and the fracturing of the formation has been completed, it is, of course, desirable to remove or reduce the viscosity of the fluid from the formation to allow hydrocarbon production through the new fractures. Generally, this achieved by "breaking" or degrading the gel or emulsion or, in other words, by converting the fracturing fluid into a low viscosity fluid by degrading the gel or other thickening agents. Breaking a gelled emulsified fracturing fluid has commonly been obtained by adding "breaker", that is, a viscosity-reducing agent, to the subterranean formation at the desired time. The reduced viscosity facilitates the flow back to the surface and the flow of produced fluid through the proppant pack towards the wellbore.

Enzymes have been used successfully as breakers for fracturing fluids for many years. Enzymes are polymer specific, environmentally benign, easy to handle, miscible in the fluid, equipment friendly and not consumed since they act as catalysts. Enzymes able to catalyze the depolymerisation of polymers such as polysaccharides. The main limitation of enzymes is their denaturation at high temperature and in alkaline pH environments.

Oxidizers such as peroxide, are also used as breakers for fracturing fluids. Some advantages of enzymes are not present when utilizing oxidizers as breakers, as oxidizers are not environmentally benign, equipment friendly, and are consumed during the degradative reaction. However, oxidizers are far more durable than enzymes, being able to degrade viscous fracturing fluid at extreme temperatures and pH environments.

In some applications viscoelastic surfactants such as viscoelastic quaternary ammonium are used as a thickener and an alcohol, an amine or carboxylic or dicarboxylic acid incorporating long hydrocarbon chains are used as breakers for the surfactants.

Previous attempts to carry the enzymes or breakers or oxidizers into fluids use particulates, such as carbon black. However, the extreme strength of the carbon nanotubes described herein provides a unique level of protection to transported enzymes; furthermore, the size and shape of the carbon nanotubes described herein enables better access to nano-porous shale formations, so allowing better breakdown of viscous fracturing fluids before removal. The present invention is applicable to many of the fluids used in the recovery of hydrocarbons from subterranean formation such as drilling fluids, completion fluids, work over fluids, packer fluids, fracturing fluids, diverting fluids, acidizing fluids, conformance or permeability control fluids, and the like.

One embodiment of the present invention is a composition useful for treating hydraulic fracturing fluids, preferably at least one aqueous fluid, comprising a plurality of discrete carbon nanotubes, preferably discrete multi-wall carbon nanotubes, wherein the discrete carbon nanotubes comprise an interior and exterior surface, each surface comprising an interior surface oxidized species content and an exterior surface oxidized species content, and at least one degradative molecule that is attached on the interior or exterior surface of the plurality of discrete carbon nanotubes. Preferably, the degradative molecule is at least one enzyme, especially wherein the enzyme is attached via Van der Waals, ionic, or covalent bonding. The degradative molecule can be at least one oxidizer, preferably wherein the oxidizer is attached via Van de Waals, ionic, or covalent bonding. Preferably, the oxidizer is selected from the group consisting of peroxides, chlorides, sulfates, and persulfates.

Another aspect of the invention is a composition useful for treating aqueous fluids comprising a plurality of discrete carbon nanotubes, wherein the discrete carbon nanotubes comprise an interior and exterior surface, each surface comprising an interior surface oxidized species content and an exterior surface oxidized species content, and at least one biocide that is attached on the interior or exterior of the discrete carbon nanotubes.

Other aspects of the invention include use of the inventive compositions comprising the degradative molecule as a targeting, sequestering and/or labeling agent in ground water remediation and/or as a targeting, sequestering and/or labeling agent in subterranean earth oil field drilling operations and/or ground water remediation in said drilling operations.

The compositions described herein can be used as an ion transport. Various species or classes of compounds/drugs/chemicals which demonstrate this ion transport effect can be used, including ionic, some non-ionic compounds, hydrophobic or hydrophilic compounds. The new carbon nanotubes disclosed herein are also useful in ground water remediation wherein the nanotubes can carry chemicals inside the inner wall that can be released once the nanotubes are in the ground avoiding chemical loss due to absorbance by ground material until the chemicals are where they are needed. The compositions comprising the novel discrete targeted oxidized carbon nanotubes can also be used as a component in, or as, a sensor. The compositions disclosed herein can also be used as a component in, or as, drug delivery or controlled release formulations. The amount of oxidation inside the nanotubes affects the amount of the drug that can be loaded inside the carbon nanotube depending on the structure of the drug. The pH of the drug affects the amount of drug that can be loaded depending on the pH and the chemical structure of the drug and the inside of the nanotube. Batteries comprising the compositions disclosed herein are also useful. Such batteries include lithium, nickel cadmium, or lead acid types. Formulations comprising the compositions disclosed herein can further comprise an epoxy, a polyurethane, or an elastomer. Such formulations can be in the form of a dispersion. The formulations can also include nanoplate structures. The compositions can further comprise at least one hydrophobic material in contact with at least one interior surface.

Discrete carbon nanotubes having specific properties can also be used in payload or drug molecule delivery, especially for use in the human body. The open ended multi-wall discrete carbon nanotubes preferably comprise at least one end having attached thereto a bio-compatible polymer, amino acid, protein or peptide.

For a more complete understanding of the present disclosure, and the advantages thereof, reference is now made to the following descriptions describing specific embodiments of the disclosure.

DETAILED DESCRIPTION OF THE INVENTION

In the following description, certain details are set forth such as specific quantities, sizes, etc., so as to provide a thorough understanding of the present embodiments disclosed herein. However, it will be evident to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

While most of the terms used herein will be recognizable to those of ordinary skill in the art, it should be understood, however, that when not explicitly defined, terms should be interpreted as adopting a meaning presently accepted by those of ordinary skill in the art. In cases where the construction of a term would render it meaningless or essentially meaningless, the definition should be taken from Webster's Dictionary, 3rd Edition, 2009. Definitions and/or interpretations should not be incorporated from other patent applications, patents, or publications, related or not.

Functionalized carbon nanotubes of the present disclosure generally refer to the chemical modification of any of the carbon nanotube types described hereinabove. Such modifications can involve the nanotube ends, sidewalls inside and/or outside, or both. Chemical modifications may include, but are not limited to covalent bonding, ionic bonding, chemisorption, intercalation, surfactant interactions, polymer wrapping, cutting, solvation, and combinations thereof. In some embodiments, the carbon nanotubes may be functionalized before, during and after being individualized or exfoliated.

Any of the aspects disclosed in this application with discrete carbon nanotubes may also be modified within the spirit and scope of the disclosure to substitute other tubular nanostructures, including, for example, inorganic or mineral nanotubes. Inorganic or mineral nanotubes include, for example, silicon nanotubes, boron nitride nanotubes and carbon nanotubes having heteroatom substitution in the nanotube structure. The nanotubes may include or be associated with organic or inorganic elements such as, for example, carbon, silicon, boron and nitrogen. Association may be on the interior or exterior of the inorganic or mineral nanotubes via Van der Waals, ionic or covalent bonding to the nanotube surfaces.

Bundled Carbon Nanotubes

As manufactured carbon nanotubes are obtainable in the form of bundles or entangled agglomerates and can be obtained from different sources, such as CNano Technology, Nanocyl, Arkema, and Kumho Petrochemical, to make discrete carbon nanotubes. An acid solution, preferably nitric acid solution at greater than about 60 weight % concentration, more preferably above 65% nitric acid concentration, can be used to prepare the carbon nanotubes for later shear to make the discrete tubes. Mixed acid systems (e.g. nitric and sulfuric acid) as disclosed in US 2012-0183770 A1 and US 2011-0294013 A1, the disclosures of which are incorporated herein by reference, can be used to produce discrete, oxidized carbon nanotubes from as-made bundled or entangled carbon nanotubes. The carbon nanotubes may be used consistent with the methods described in U.S. Pat. No. 7,992,640; U.S. Application No. 2015/0368541; and U.S. Application No. 2014/0014586, all of which are incorporated herein by reference.

As-made carbon nanotubes using metal catalysts such as iron, aluminum or cobalt can retain a significant amount of the catalyst associated or entrapped within the carbon nanotube, as much as five weight percent or more. These residual metals can be deleterious in such applications as electronic devices because of enhanced corrosion or can interfere with the vulcanization process in curing elastomer composites. Furthermore, these divalent or multivalent metal ions can associate with carboxylic acid groups on the carbon nanotube and interfere with the discretization of the carbon nanotubes in subsequent dispersion processes. In other embodiments, the oxidized carbon nanotubes comprise a residual metal concentration of less than about 25000 parts per million, ppm, and preferably less than about 5000 parts per million. The metals composition and concentration can be conveniently determined using energy dispersive X-ray spectroscopy or thermogravimetric methods.

The composition of discrete carbon nanotubes in a plasticizer can be used as an additive to a variety of compounds and composites to improve the mechanical properties, thermal and electrical conductivity. An example is as an additive in rubber compounds used to fabricate rubber components in oil field applications such as seals, blowout preventers and drill motors with improved wear resistance, tear strength and thermal conductivity. Another example is as an additive in rubber compounds used to fabricate tires, seals and vibration dampeners. By selecting the appropriate plasticizer the additive has utility in compounding and formulating in thermoplastics, thermosets and composites.

Minimal Acid Oxidation (MAO)

The present application discloses a novel method of manufacture of carbon nanotubes with minimal acid oxidation. Acid oxidation of carbon nanotubes as previously described in various Bosnyak et al. patents (e.g., U.S. Pat. Nos. 8,475,961, 8,993,161 and 9,065,132, the disclosures of each of which are incorporated herein by reference) and patent applications, is done by suspension of the carbon nanotubes in acid at concentrations from 2 to 4% CNT by weight in acid. After oxidation, the acid is removed by some means of solid/fluid separation such as filtration. The amount of acid removed ranges from 60% to 70% with about 30% to 40% becoming waste. Centrifugation can reduce the waste to 10%; however, centrifugation is an expensive and high maintenance process.

In the MAO process, the concentration of carbon nanotubes in the reaction process is increased. Using nitric acid (65% concentration) mixtures of high CNT concentration such as 43% CNT by weight in nitric acid has the unexpected consistency of a flowable powder. When the oxidation process is complete, the acid is not removed but diluted with water and then filtered during the washing process. This eliminates the step of acid filtration for retrieval of acid. The amount of acid wasted in the washing process is significantly less than in the process utilizing more acid with less nanotubes in the reaction.

Minimal acid oxidation (MAO) uses a wet powder process to eliminate excess acid. In MAO process the nitric acid (65% concentration) is mixed with the CNT to a concentration of 43.2% by weight CNT to acid. It is then subjected to heating to 90° C. The amount of oxidation and removal of metals is controlled by the time and temperature of reaction. Table 1 is an illustrative example. Note that the nitric acid waste, when utilizing the MAO process, is only 1.3 times the weight of the CNT as compared to 9.6 times the weight of the CNT with 70% acid removal efficiency or 3.2 time the weight of the CNT with 90% acid removal efficiency. This significantly reduces the cost of production by decreasing the amount of waste acid per mass of CNT, decreasing waste disposal and removing the filtration of acid step.

TABLE 1

|  | High Acid Method (Assuming 70% filter efficiency | High Acid Method (Assuming 90% filter efficiency | Minimal Acid method. |
| --- | --- | --- | --- |
| Reaction Mixture | 3 parts CNT to 97 part HNO3 by weight | 3 parts CNT to 97 part HNO3 by weight | 43 parts CNT to 56 parts HNO3 by weight |
| After filtration | 3 parts CNT to 29 parts HNO3 by weight | 3 parts CNT to 9.7 parts HNO3 by weight | Not Required |
| Acid lost due to water wash | 9.6 times the weight of CNT | 3.2 times the weight of CNT | 1.3 times the weight of CNT |

In addition to the waste saving, the MAO process removes the same amount of metal impurities from the tubes and the tube length, tube length distribution and detangling quality are the same as the higher acid method. In three scaled-up laboratory production runs, MAO resulted in a higher percentage oxidization of carbon nanotubes compared to the high acid method (2.59, 2.99, 4.01% Ox with MAO v. 1.9% Ox with higher amount of acid). Thus, even with relatively inefficient laboratory mixing, MAO resulted in reproducible oxidation and by control of the temperature and time, the amount of oxidation and amount of residual metals removed is controlled. The carbon nanotubes produced by MAO have the same kinds of functionalities, and the increase in oxidation does not change the species but increases the amount mm/g functionality of each species. MAO provides advantages by eliminating acid filtration, reducing the amount of acid wasted, giving greater control of percent oxidation, achieving increased oxidation and reducing residue in less time. The increased oxidation in MAO also enables further downstream chemistry modification.

In various embodiments, a plurality of carbon nanotubes is disclosed comprising single wall, double wall or multi wall carbon nanotube fibers having an aspect ratio of from about 10 to about 500, preferably from about 40 to about 200, and an overall (total) oxidation level of from about 1 weight percent to about 15 weight percent, preferably from about 1 weight percent to about 10 weight percent, more preferably from about 1 weight percent to 5 weight percent, more preferably from about 1 weight percent to 3 weight percent. The oxidation level is defined as the amount by weight of oxygenated species covalently bound to the carbon nanotube divided by the total weight mass of oxygenated nanotubes. The thermogravimetric method for the determination of the percent weight of oxygenated species on the carbon nanotube involves taking about 7-15 mg of the dried oxidized carbon nanotube and heating at 5° C./minute from 100 degrees centigrade to 700 degrees centigrade in a dry nitrogen atmosphere. The percentage weight loss from 200 to 600 degrees centigrade is taken as the percent weight loss of oxygenated species. The oxygenated species can also be quantified using Fourier transform infra-red spectroscopy, FTIR, particularly in the wavelength range 1730-1680 $cm^{-1}$.

The carbon nanotubes can have oxidation species comprising carboxylic acid or derivative carbonyl containing species and are essentially discrete individual nanotubes, not entangled as a mass. Typically, the amount of discrete carbon nanotubes after completing the process of oxidation and shear is by a far a majority (that is, a plurality) and can be as high as 70, 80, 90 or even 99 percent of discrete carbon nanotubes, with the remainder of the tubes still partially entangled in some form. Complete conversion (i.e., 100 percent) of the nanotubes to discrete individualized tubes is most preferred. The derivative carbonyl species can include phenols, ketones, quaternary amines, amides, esters, acyl halogens, carboxylic groups, hydroxyl groups, monovalent metal salts and the like, and can vary between the inner and outer surfaces of the tubes. For example, one type of acid can be used to oxidize the tubes exterior surfaces, followed by water washing and induced shear, thereby breaking and separating the tubes. If desired, the formed discrete tubes, having essentially no (preferably <½%, more preferably zero) interior tube wall oxidation can be further oxidized with a different oxidizing agent, or even the same oxidizing agent as that used for the tubes' exterior wall surfaces at a different concentration, resulting in differing amounts—and/or differing types—of interior and surface oxidation.

In certain embodiments the interior surface oxidized species content may be different from the exterior surface oxidized species content by greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, greater than 99%, or 100% greater. In other embodiments, the interior surface oxidized species content may be different from the exterior surface oxidized species content by less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, less than 95%, less than 100%.

In further embodiments, the exterior surface oxidized species content may be different from the interior surface oxidized species content by greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, greater than 99%, or 100% greater. In other embodiments, the exterior surface oxidized species content may be different from the interior surface oxidized species content by less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, less than 95%, less than 100%.

In some embodiments, the discrete carbon nanotubes with an average length of 900 nm, outside diameter of 10-15 nm and inside diameter of 3-6 nm, can have about 0.1 mMoles/g to about 0.4 mMoles/g tubes carboxylic groups (COOH). The concentration of OH groups can be from about 0.1 mMoles/g to about 0.4 mMoles/g and the concentration of lactones can be from about 0.05 mMoles/g to about 0.3 mMoles/g. The total surface area can be from 200 m2/g to 280 m2/g. The bulk conductivity of a dried pressed mat of the discrete tubes can have be from about 1 to 6 ohms. The density of the discrete tubes can be 1.8 to 1.9 g/cm$^2$.

General Process to Produce Discrete Carbon Nanotubes Having Targeted Oxidation

A mixture of 0.5% to 5% carbon nanotubes, preferably 2%, by weight is prepared with CNano grade Flotube 9000 carbon nanotubes and 65% nitric acid. While stirring, the acid and carbon nanotube mixture is heated to 70 to 90 degrees C. for 2 to 4 hours. The formed oxidized carbon nanotubes are then isolated from the acid mixture. Several methods can be used to isolate the oxidized carbon nanotubes, including but not limited to centrifugation, filtration, mechanical expression, decanting and other solid—liquid separation techniques. MAO can be used to eliminate this stage as discussed above. The residual acid is then removed by washing the oxidized carbon nanotubes with an aqueous medium such as water, preferably deionized water, to a pH of about 3 to 4.

The carbon nanotubes are then suspended in water at a concentration of 0.5% to 4%, preferably 1.5% by weight. The solution is subjected to intensely disruptive forces generated by shear (turbulent) and/or cavitation with process equipment capable of producing energy densities of $10^6$ to $10^8$ Joules/m$^3$. Equipment that meets this specification includes but is not limited to ultrasonicators, cavitators, mechanical homogenizers, pressure homogenizers and microfluidizers (Table 2). One such homogenizer is shown in U.S. Pat. No. 756,953, the disclosure of which is incorporated herein by reference. After shear processing, the oxidized carbon nanotubes are discrete and individualized carbon nanotubes. Typically, based on a given starting amount of entangled as-received and as-made carbon nanotubes, a plurality of discrete oxidized carbon nanotubes results from this process, preferably at least about 60%, more preferably at least about 75%, most preferably at least about 95% and as high as 100%, with the minority of the tubes, usually the vast minority of the tubes remaining entangled, or not fully individualized.

Another illustrative process for producing discrete carbon nanotubes follows: A mixture of 0.5% to 5% carbon nanotubes, preferably 3%, by weight is prepared with CNano Flotube 9000 grade carbon nanotubes and an acid mixture that consists of 3 parts by weight of sulfuric acid (97% sulfuric acid and 3% water) and 1 part by weight of nitric acid (65-70 percent nitric acid). The mixture is held at room temperature while stirring for 3-4 hours. The formed oxidized carbon nanotubes are then isolated from the acid mixture. Several methods can be used to isolate the oxidized carbon nanotubes, including but not limited to centrifugation, filtration, mechanical expression, decanting and other solid—liquid separation techniques. MAO can be used to eliminate this stage as discussed above. The acid is then removed by washing the oxidized carbon nanotubes with an aqueous medium, such as water, preferably deionized water, to a pH of 3 to 4.

The oxidized carbon nanotubes are then suspended in water at a concentration of 0.5% to 4%, preferably 1.5% by weight. The solution is subjected to intensely disruptive forces generated by shear (turbulent) and/or cavitation with process equipment capable of producing energy densities of $10^6$ to $10^8$ Joules/m$^3$. Equipment that meet this specification includes but is not limited to ultrasonicators, cavitators mechanical homogenizers, pressure homogenizers and microfluidizers (Table 2). After shear and/or cavitation processing, the oxidized carbon nanotubes become oxidized, discrete carbon nanotubes. Typically, based on a given starting amount of entangled as-received and as-made carbon nanotubes, a plurality of discrete oxidized carbon nanotubes results from this process, preferably at least about 60%, more preferably at least about 75%, most preferably at least about 95% and as high as 100%, with the minority of the tubes, usually the vast minority of the tubes remaining entangled, or not fully individualized.

Nanotube-Mediated Controlled Delivery of Degradative Enzymes

The viscous fracturing fluid, which can be partially or totally crosslinked, or uncrosslinked (linear), and the related filter cake made on the face of the rock must be broken in order to conduct hydrocarbon extraction. Oxidizers, enzymes, and acids are typical degradative molecules (also known as breakers) used depending on different fracturing conditions. Polymers are cleaved into small molecular weight fragments by breakers. The present application discloses the use of the functionalized carbon nanotubes described herein to treat the fracturing fluid, providing improved controlled delivery of enzymes used to degrade down viscous fracturing fluid components. By treating fracturing fluid, it is meant that the hydraulic fracturing fluid's viscosity is decreased by at least 10%, to a a maximum of 4 orders of magnitude, and preferentially reduce the fluid's viscosity as much as possible. For example, to calculate reduction in viscosity, if the starting viscosity of a fracturing fluid is 1000 centipoise (cP) and is treated with a breaking agent, the fluid's viscosity will decrease by at least 10%, to 900 cP, or to a maximum down to 1 cP (a change of 3 orders of magnitude).

This use provides customizable delivery time scales, improvements to shear force resistance, and better distribution to tight shale nano-porous networks in oil-field applications. The ability of carbon nanotubes described herein provides a unique level of controlled diffusion release, more uniformly releasing the oxidizing breakers throughout the nano-porous shale formations, allowing better breakdown of viscous fracturing fluids. The functionalized carbon nanotubes act as protective carriers to deliver degradative chemicals, for example enzymes, into fractured formations, which results in better enzyme dispersion, lifetime and controllability. The functionalized carbon nanotubes can also be used in any situation where a time-controlled delivery is critical to the operation/field, e.g., delivery of anti-corrosives over a long time, delivery of biocides in coatings, wastewater cleanup (delivery of biocides, neutralizing agents, etc). Contaminants that can be treated in various manners by the carbon nanotubes herein and that may be found in oilfield produced water, flowback water, and aqueous refinery effluents can include, at varying levels, materials such as: (1) dispersed oil and grease, if not removed by mechanical pretreatment separators can clog post-treatment equipment; (2) benzene, toluene, ethylbenzene and xylenes (BTEX), a volatile fraction; (3) water-soluble organics; (4) sparingly soluble nonvolatile organics, including aromatics with molecular weights higher than BTEX but lower than asphaltenes; (5) treatment chemicals, such as drilling, completion, stimulation and production chemicals; (6) produced solids like clays, silicates and metal sulfides, usually removed by mechanical separators; and (7) total dissolved solids including metals, a particular problem because many metals are considered toxic. Petroleum industry waste water also includes water used for hydraulic fracturing.

The discrete carbon nanotubes described herein can be loaded, either on the surface, internally, or both, with a currently-used degradative enzyme. Using the carbon nanotubes described herein prevents the enzyme from being denatured, sheared, or damaged prematurely in the downhole pumping process. The technologies currently being used in the field do not make use of discrete carbon nanotubes, and do not have the particular size, shape, and aspect ratio of the carbon nanotubes described herein. One of ordinary skill will understand that various methods may be used to attach/bind/load enzymes onto or into the carbon nanotubes described herein as payloads for delivery; no particular method should be considered limiting of the present invention. One of ordinary skill will also understand that various methods of entrapping enzymes until selectively freeing them may also be used; no particular method should be considered limiting of the present invention. The entrapped enzymes may be protected from damage by the carbon nanotubes during transportation to a suitable site for the release of the enzymes. One of ordinary skill will understand that the present application also encompasses selectively controlled nanotube-mediated delivery of degradative enzymes. One of ordinary skill will understand that there are various mechanisms of degrading the attachment/binding/loading of entrapped material so that enzymes may freely perform their desired function in the field; no particular mechanism should be considered limiting on the present invention.

Enzymes are generally breakers of the class hemicellulose ("hemicellulases"); unlike oxidizing agents, they are not consumed after reaction. Enzymes are very cheap but sensitive to pH and temperature. They often denature at elevated temperatures or extreme pH values. Enzymes could have increased lifetime at high pressure. Examples of enzymes that may be delivered by the carbon nanotubes described herein include GBW-12CD (a commercially available hemicellulose enzyme concentrate), LEB-H (a commercially available high pH enzyme breaker), gammanase (a commercial extract of *Aspergillus niger* consisting primarily of a mixture of endo-β-mannanase and α-galactosidase), endo-mannanase, β-mannanase, pectinase from *Aspergillus aculaceatus*, or Econo Gelbreak-EL2X (Economy Polymers and Chemicals, Houston, Tex., Lot No. L0901415). U.S. Pat. No. 5,201,370 discloses an enzyme breaker for galactomannan-based fracturing fluids wherein the enzyme breaker is effective to degrade the polymer gel at temperatures between 50° F. and 180° F. A hemicellulase enzyme has been disclosed in WO 91/18974, having a range of activity from 0° C. (32° F.) to 90° C. (194° F.); other enzymes are disclosed in U.S. Pat. Nos. 5,165,477, and 5,441,109, all of which are incorporated herein by reference. A hemicellulase enzyme can be produced in accordance with the methods disclosed in WO 91/18974. A detailed description and classification of known enzymes is provided in the reference entitled Enzyme Nomenclature (1984): Recommendations of the Nomenclature Committee of the International Union of Biochemistry on the Nomenclature and Classification of Enzyme-Catalysed Reactions (Academic Press 1984) (hereinafter referred to as "Enzyme Nomenclature (1984)"), the disclosure of which is fully incorporated by reference herein. According to Enzyme Nomenclature (1984), enzymes can be divided into six classes, namely (1) Oxidoreductases, (2) Transferases, (3) Hydrolases, (4) Lyases, (5) Isomerases, and (6) Ligases. Each class of enzyme may be further divided into subclasses and by action, etc, any one of which may be chosen by one of ordinary skill according to the appropriate needs of the circumstances. One of ordinary skill will understand that the choice of enzyme to be loaded on the carbon nanotubes is not limiting on the present invention.

Encapsulated enzyme breakers delay the release of active enzyme into the fracturing fluid to minimize the early effects of the breaker on the fluid. This delay allows higher breaker concentrations to be used without compromising the proppant transport capacity of the fracturing fluid. The solid breaker also may be concentrated in the fracture and not lost to the formation during fluid leak-off. The carbon nanotubes herein may be used to form encapsulated enzyme breakers. In embodiments, specifically selected or designed polypeptides and proteins can be used as enzymes to be delivered by carbon nanotubes in accordance with these systems and methods.

In some down hole and ground water remediation applications, the use of a tracer in the injected fluid is used to obtain information about the hydrocarbon reservoir or other hydrogeological structures. A tracer may be a dye, fluroescer, or other chemical that can be detected using spectroscopic analytical methods such as UV-visible, florescence of phosphorescence. A tracer may be a radioisotope or radionuclide, genetically coded material or chemical with distinctive features which enables it to be distinguished by another analytical technique such as GC-MS. It is now discovered that such tracers or dyes are useful when placed in contact with the discrete nanotubes described herein. The tracers and/or dyes can be in contact with, or sometimes attached to, either the exterior or interior surface, or both, of the discrete tubes.

Biocides are a wide variety of bioactive organic chemicals which have been developed for disinfection, sterilization, and preservation purposes, including quaternary ammonium compounds, alcoholic and phenolic compounds, aldehydes, halogen-containing compounds, quinoline and isoquinoline derivatives, heterocyclic compounds, and peroxygens. Biocides are often used in hydraulic fracturing fluid formulations (see, e.g., Environ. Sci. Technol. 2015, 49, 16-32, which is incorporated herein by reference). Such biocides include lytic biocides, cationic quaternary ammonium/ amine compounds ("QACs" or "quats") didecyl dimethylammonium chloride (DDAC or decanaminium, alkyldimethylbenzylammonium chloride (ADBAC, benzalkonium chloride, BAC, BC, or benzenemethanaminium), dibromonitrilopropionamide, chlorine dioxide, tributyl tetradecyl phosphonim chloride, alkyl dimethyl benzyl phosphonim chloride, sodium hypchlorite, dazomet, dimethyloxazolidone, trimetyloxazolidine, N-bromosuccinimide, bronopol, peracetic acid, electrophilic biocides, glutaraldehyde, tetrakis(hydroxymethyl)phosphonium sulfate (THPS), chloromethylisothiazolinone (CMIT, or MCI, 5-chloro-2-methyl-3 (2H)-isothiazolinone) or methylisothiazolinone (MIT, or MI, 2-methyl-3(2H)-isothiazolinone). One of ordinary skill will understand that the carbon nanotubes disclosed herein may be used in conjunction with any of these biocides; the choice of biocide is not limiting on the present invention.

In some embodiments, the modification to the interior or exterior surface of a carbon nanotube can be a cationic material that can be deposited on the substrate by covalent, ionic, hydrophobic, hydrostatic interactions, or by saturation, coating, or deposition from a solution. Examples of modifying agents include cationic polymers, cationic surfactants, and cationic covalent modifiers. Cationic polymers can include linear or branched polyethylenimine, poly-DADMAC, epichlorohydrin/DMA condensation polymers, amine/aldehyde condensates, chitosan, cationic starches, styrene maleic anhydride imide (SMAI), and the like. Cationic surfactants can include cetyltrimethylammonium bromide (CTAB), alkyldimethylbenzyl quats, dialkylmethylbenzylammonium quats, and the like. Cationic covalent modifiers can include quaternization reagents like Dow Q-188 or organosilicon quaternary ammonium compounds. Examples of the organosilicon quaternary ammonium compounds are 3-trihydroxysilylpropyldimethylalkyl ($C_6$-$C_{22}$) ammonium halide, 3-trimethoxysilylpropyldimethylalkyl ($C_6$-$C_{22}$) ammonium halide, 3-triethoxysilylpropyldimethylalkyl ($C_6$-$C_{22}$) ammonium halide, and the like. In other embodiments, the modification to the carbon nanotubes can be an oxidizing compound such as potassium permanganate, sodium hypochlorite, and sodium percarbonate. The modified carbon nanotube can be coated with a hydrophobic layer to cause slow release of the modifying agent.

The modifying agents (also referred to as "payload") are preferably capable of being immobilized onto the carbon nanotubes by mechanisms of bonding, complexing, or adhering. In embodiments, the agents can be a polymer that has an affinity for the surface of the substrate. In embodiments, the agents can be applied to the substrate in the form of a solution. In embodiments, the agents are insoluble in water after it is affixed to the substrate. In embodiments, the agents have a metal chelating group, and can be deposited on the substrate by covalent, ionic, hydrophobic or hydrostatic interactions, or by saturation, coating, or deposition from a solution. Examples of agents include compounds or polymers containing anionic chelant functional groups selected from the list comprising phosphate, phosphonate, xanthate, dithiocarbamate, hydroxamate, carboxylate, sulfate, and sulfide. Examples of agents include fatty acids, fatty amides, and vinyl polymers with the above listed chelant groups. Examples of agents based on vinyl polymers include comonomers of vinylphosphonic acid, vinylidenediphosphonic acid, 2-acrylamido-2-methylpropane sulfonic acid (2-AMPS), acrylamide-N-hydroxamic acids, itaconic acid, maleic acid, and salts thereof. In embodiments, inorganic salts such as ferric chloride tetrahydrate can be used as agents.

Aqueous solubility of payload substances is an important parameter in pre-formulation studies of a payload. Various payload molecules may be sparingly water-soluble and pose challenges for formulation and administration. Organic solvents or oils and additional surfactants to create dispersions can be used. If the payload molecule is easily dissolved or dispersed in an aqueous media, the filter cake need not be dried. If the payload molecule is not easily dissolved or dispersed in aqueous media, the filter cake is first dried at 80° C. in vacuum to constant weight. The payload molecule in the liquid media at the desired concentration is added to the discrete carbon nanotubes and allowed several hours to equilibrate within the tube cavity. The mixture is then filtered to form a cake, less than about 1 mm thickness, then the bulk of the payload solution not residing within the tubes are removed by high flow rate filtration. The rate of filtration is selected so that little time is allowed for the payload molecules to diffuse from the tube cavity. The filter cake plus payload molecule is then subjected to an additional treatment if desired to attach a large molecule such an aqueous solution of a biopolymer, an amino acid, protein or peptide, depending on the intent of the user.

In one aspect the payload is a composition comprising: a plurality of functionalized discrete, open ended multi-wall carbon nanotubes; wherein the functionalized discrete carbon nanotubes are aqueous-dispersible, and at least one type of payload molecule, the majority (preferably >60%, more preferably >75%, especially >95%) of which are located inside the discrete open ended multi-wall carbon nanotubes (and wherein minimal drug molecules (e.g., <20%, preferably <10%, more preferably <5%) are located outside the walls of the discrete open ended multi-wall carbon nanotubes). The functionalizing groups are selected from the group consisting of bio-compatible surfactants. Preferred bio-compatible surfactants include, but not limited to, PLA (polylactic acid), PVOH (polyvinyl alcohol), PEO (polyethylene oxide), PGLA (polyglycolic acid), CMC (carboxy methyl cellulose), amino acids, peptides, polysacharides and proteins (e.g., albumin).

At least one type of payload molecule is preferably at least partially released from the open ended multi-wall discrete carbon nanotubes by a mechanism comprising electromagnetic radiation exposure (e.g., MRI (Magnetic Resonance Imaging)), local pH changes, electrolyte balance, or biological digestion of the biopolymer coat. Based on desired rate of payload delivery 10% by weight or less of the discrete carbon nanotubes MR of the formulation can comprise L/D of about 100 to 200 and about 30% or more of the discrete carbon nanotubes MR of the formulation can comprise L/D of 40 to 80. The L/D of the discrete carbon nanotubes can be a unimodal distribution, or a multimodal distribution (such as a bimodal distribution). The multimodal distributions can have evenly distributed ranges of aspect ratios (such as 50% of one L/D range and about 50% of another L/D range). The distributions can also be asymmetrical—meaning that a relatively small percent of discrete nanotubes can have a specific L/D while a greater amount can comprise another aspect ratio distribution.

Yet another method of at least partial release of the payload molecule, especially for drug delivery, is to attach magnetic particles or compounds to the discrete carbon nanotubes and then steer the tubes comprising the payload or drug to the desired location using magnetic influences, such as magnetic resonance imaging (MRI). Such a technique is suggested in *Physics Letters* A by Kezheng Chen and Ji Ma from Quingdou University of Science and Technology, Quingdou, China and uses superparamagnetic crystals. These crystals include iron oxides that, when small enough (such as $1 \times 10^{-6}$ mm to $10 \times 10^{-6}$ mm in diameter, react to temperature changes to influence crystal magnetism. Such a system is known as supermagnetism.

The plurality of functionalized discrete open ended multi-wall carbon nanotubes preferably comprises tube lengths of varying lengths. The tube length distribution may be monomodal, bimodal or multimodal. For tube length distributions comprising at least 2 groups of lengths, preferred is wherein each group's tube length varies on average by at least about 10% from the other group's average tube length to control drug release rates. Different length distributions may contain different payload molecules. The plurality of functionalized discrete open ended multi-wall carbon nanotubes comprises an average aspect ratio of from about 25 to about 200, preferably 25-100 and most preferably 40-120. The plurality of functionalized discrete open ended multi-wall carbon nanotubes can comprise 0.01 to 99% by weight of the formulation, preferably 0.1 to 99, more preferably 0.25 to 95% by weight of the formulation.

The following examples are intended to be illustrative of certain embodiments of the present application, and are not intended to be limiting in any way.

EXAMPLES

Example 1

ENTANGLED OXIDIZED AS MWCNT—3 Hour (oMWCNT-3)

One hundred milliliters of >64% nitric acid is heated to 85° C. To the acid, 3 grams of as-received, multi-walled carbon nanotubes (C9000, CNano Technology) are added. The as-received tubes have the morphology of entangled balls of wool. The mixture of acid and carbon nanotubes are mixed while the solution is kept at 85° C. for 3 hours and is labeled "oMWCNT-3". At the end of the reaction period, the MWCNT-3 are filtered to remove the acid and washed with reverse osmosis (RO) water to pH of 3-4. After acid treatment, the carbon nanotubes are still entangled balls. The tubes are dried at 60° C. to constant weight.

Example 2

ENTANGLED OXIDIZED AS MWCNT—6 Hour (oMWCNT-6)

One hundred milliliters of >64% nitric acid is heated to 85° C. To the acid, 3 grams of as-received, multi-walled carbon nanotubes (C9000, CNano Technology) are added. The as-received tubes have the morphology of entangled balls of wool. The mixture of acid and carbon nanotubes are mixed while the solution is kept at 85° C. for 6 hours and is labeled "oMWCNT-6". At the end of the reaction period, the oMWCNT-6 are filtered to remove the acid and washed with reverse osmosis (RO) water to pH of 3-4. After acid treatment, the carbon nanotubes are still entangled balls. The tubes are dried at 60° C. to constant weight.

Example 3

DISCRETE CARBON NANOTUBE—OXIDIZE OUTERMOST WALL (out-dMWCNT)

In a vessel, 922 kilograms of >64% nitric acid is heated to 83° C. To the acid, 20 kilograms of as received, multi-walled carbon nanotubes (C9000, CNano Technology) is added. The mixture is mixed and kept at 83° C. for 3 hours. After the 3 hours, the acid is removed by filtration and the carbon nanotubes washed with RO water to pH of 3-4. After acid treatment, the carbon nanotubes are still entangled balls with few open ends. While the outside of the tube is oxidized forming a variety of oxidized species, the inside of the nanotubes have little exposure to acid and therefore little oxidization. The oxidized carbon nanotubes are then suspended in RO water at a concentration of 1.5% by weight. The RO water and oxidized tangled nanotubes solution is subjected to intensely disruptive forces generated by shear (turbulent) and/or cavitation with process equipment capable of producing energy densities of $10^6$ to $10^8$ Joules/$m^3$. The resulting sample is labeled "out-dMWCNT" which represents outer wall oxidized and "d" as discrete. Equipment that meet this shear includes but is not limited to ultrasonicators, cavitators, mechanical homogenizers, pressure homogenizers, and microfluidizers (see Table 2). It is believed that the shear and/or cavitation processing detangles and discretizes the oxidized carbon nanotubes through mechanical means that result in tube breaking and opening of the ends due to breakage particularly at defects in the CNT structure which is normally a 6 member carbon rings. Defects happen at places in the tube which are not 6 member carbon rings. As this is done in water, no oxidation occurs in the interior surface of the discrete carbon nanotubes.

A comparative table (Table 3 below) shows the levels of oxidation of different batches of carbon nanotubes that have been oxidized either just on the outside (Batch 1, Batch 2, and Batch 3), or on both the outside and inside (Batch 4). Batch 1 (oMWCNT-3 as made in Example 1 above) is a batch of entangled carbon nanotubes that are oxidized on the outside only when the batch is still in an entangled form (Table 3, first column). Batch 2 (oMWCNT-6 as made in Example 2 above) is also a batch of entangled carbon nanotubes that are oxidized on the outside only when the batch is still in an entangled form (Table 3, second column). The average percent oxidation of Batch 1 (2.04% Ox) and Batch 2 (2.06% Ox) are essentially the same. Since the difference between Batch 1 (three hour exposure to acid) and Batch 2 (six hour exposure to acid) is that the carbon nanotubes were exposed to acid for twice as long a time in Batch 2, this indicates that additional exposure to acid does not increase the amount of oxidation on the surface of the carbon nanotubes.

TABLE 2

| Homogenizer Type | Flow Regime | Energy Density ($J\text{-}m^{-3}$) |
| --- | --- | --- |
| Stirred tanks | turbulent inertial, turbulent viscous, laminar viscous | $10^3\text{-}10^6$ |
| Colloid mil | laminar viscous, turbulent viscous | $10^3\text{-}10^8$ |
| Toothed - disc disperser | turbulent viscous | $10^3\text{-}10^8$ |
| High pressure homogenizer | turbulent inertial, turbulent viscous, cavitation inertial, laminar viscous | $10^6\text{-}10^8$ |
| Ultrasonic probe | cavitation inertial | $10^6\text{-}10^8$ |
| Ultrasonic jet | cavitation inertial | $10^6\text{-}10^8$ |
| Microfluidization | turbulent inertial, turbulent viscous | $10^6\text{-}10^8$ |
| Membrane and microchannel | Injection spontaneous transformation based | Low $10^3$ |

Excerpted from *Engineering Aspects of Food Emulsification and Homogenization*, ed. M. Rayner and P. Dejmek, CRC Press, New York 2015.

Example 4

DISCRETE CARBON NANOTUBE—OXIDIZED OUTER AND INNER WALL (out/in-dMWCNT)

To oxidize the interior of the discrete carbon nanotubes in example 3, 3 grams of the out-dMWCNT is added to 64% nitric acid heated to 85° C. The solution is mixed and kept at temperature for 3 hours. During this time, the nitric acid oxidizes the interior surface of the carbon nanotubes. At the end of 3 hours, the tubes are filtered to remove the acid and then washed to pH of 3-4 with RO water. This sample is labeled "out/in-dMWCNT" representing both outer and inner wall oxidation and "d" as discrete.

Oxidation of the samples of carbon nanotubes is determined using a thermogravimetric analysis method. In this example, a TA Instruments Q50 Thermogravimetric Analyzer (TGA) is used. Samples of dried carbon nanotubes are ground using a vibration ball mill. Into a tarred platinum pan of the TGA, 7-15 mg of ground carbon nanotubes are added. The measurement protocol is as follows. In a nitrogen environment, the temperature is ramped from room temperature up to 100° C. at a rate of 10° C. per minute and held at this temperature for 45 minutes to allow for the removal of residual water. Next the temperature is increased to 700° C. at a rate of 5° C. per minute. During this process the weight percent change is recorded as a function of temperature and time. All values are normalized for any change associated with residual water removal during the 100° C. isotherm. The percent of oxygen by weight of carbon nanotubes (% Ox) is determined by subtracting the percent weight change at 600° C. from the percent weight change at 200° C.

Batch 3 (Out-dMWCNT as made in Example 3 above) is a batch of entangled carbon nanotubes that were oxidized on the outside only when the batch was still in an entangled form (Table 3, third column). Batch 3 was then been made into a discrete batch of carbon nanotubes without any further oxidation. Batch 3 serves as a control sample for the effects on oxidation of rendering entangled carbon nanotubes into discrete nanotubes. Batch 3 shows essentially the same average oxidation level (1.99% Ox) as Batch 1 and Batch 2. Therefore, Batch 3 shows that detangling the carbon nanotubes and making them discrete in water opens the ends of the tubes without oxidizing the interior.

Finally, Batch 4 (Out/In-dMWCNT as made in this Example 4 herein) is a batch of entangled carbon nanotubes that are oxidized on the outside when the batch is still in an entangled form, and then oxidized again after the batch has then been made into a discrete batch of carbon nanotubes (Table 3, fourth column). Because the discrete carbon nanotubes are open ended, in Batch 4 acid enters the interior of the tubes and oxidizes the inner surface. Batch 4 shows a significantly elevated level of average oxidation (2.39% Ox) compared to Batch 1, Batch 2 and Batch 3. The significant elevation in the average oxidation level in Batch 4 represents the additional oxidation of the carbon nanotubes on their inner surface. Thus, the average oxidation level for Batch 4 (2.39% Ox) is about 20% higher than the average oxidation levels of Batch 3 (1.99% Ox). In Table 3 below, the average value of the oxidation is shown in replicate for the four batches of tubes. The percent oxidation is within the standard deviation for Batch 1, Batch 2 and Batch 3.

TABLE 3

Percent oxidation by weight of carbon nanotubes.

| | Batch 1: oMWCNT-3 % Ox | Batch 2: oMWCNT-6 % Ox | Batch 3: Out-dMWCNT % Ox | Batch 4: Out/In-dMWCNT % Ox | Difference in % Ox (Batch 4 − Batch 3) | *% difference in % Ox (Batch 4 v Batch 3) |
|---|---|---|---|---|---|---|
| | 1.92 | 1.94 | 2.067 | 2.42 | 0.353 | 17% |
| | 2.01 | 2.18 | 1.897 | 2.40 | 0.503 | 26.5% |
| | 2.18 | NM | 2.12 | 2.36 | 0.24 | 11% |
| | 2.05 | NM | 1.85 | NM | n/a | n/a |
| Average | 2.04 | 2.06 | 1.99 | 2.39 | 0.4 | 20% |
| St. Dev. | 0.108 | 0.169 | 0.130 | 0.030 | n/a | n/a |

NM = Not Measured
*% difference between interior and exterior oxidation surfaces (Batch 4 v Batch 3) = (((outside % oxidation) − (inside % oxidation)) ÷ (outside % oxidation)) × 100

An illustrative process to form a composition comprising discrete carbon nanotubes in a plasticizer is to first select a plurality of discrete carbon nanotubes having an average aspect ratio of from about 10 to about 500, and an oxidative species content total level from about 1 to about 15% by weight. Then the discrete carbon nanotubes are suspended using shear in water at a nanotube concentration from about 1% to about 10% by weight to form the nanotube water slurry. The slurry is then mixed with at least one plasticizer at a temperature from about 30° C. to about 100° C. for sufficient time that the carbon nanotubes migrate from the water to the plasticizer to form a water/nanotube and plasticizer mixture. The mixture can comprise from 70% to about 99.9% water. The bulk of the water is separated from the mixture by filtration, decanting or other means of mechanical separation. The filtered material can contain from about 50% to about 10% water. The filtered material is then dried at a temperature from about 40° C. to about 120° C. to form a dry nanotube/plasticizer mixture with less than 3% water, most preferably less than 0.5% water by weight and for some applications 0% water by weight.

Example 5

A concentrate of discrete carbon nanotubes in water with only the exterior wall oxidized as in Example 3 is diluted to a 2% by weight in deionized water. The slurry is heated to 40° C. while stirring with an overhead stirrer at 400 rpm. For every gram of discrete carbon nanotubes, 4 grams of TOTM (trioctyl trimellitate) from Sigma Aldrich is added to the stirring mixture. For 4 hours, the mixture is stirred at 750 rpm and kept at 40° C. During this time, the oil and discrete carbon nanotubes floats to the top, leaving clear water at the bottom. When this occurs, the water is separated from the TOTM/carbon nanotube mixture by decantation and filtration. The TOTM and discrete carbon nanotubes are dried in a forced air convection oven at 70° C. until residual water is removed. The result is a flowable powder. The concentration of discrete carbon nanotubes is determined by thermogravimetric means and found to be 20% (wt.) discrete carbon nanotubes and 80% TOTM.

Example 6

The discrete carbon nanotubes and plasticizer composition of Example 5 comprising 20% discrete carbon nanotubes and 80% TOTM (trioctyle trimellitate) is added at concentrations of 2 parts per hundred of discrete carbon nanotubes resin (phr) and 3 parts per hundred resin (phr) to a nitrile rubber formulation (Table 4). The oil concentration of the formulations is adjusted to compensate for the additional oil from the composition of this invention. The compound is then cured into plaques for testing. Constrained tear testing is performed using an Instron tensiometer. Constrained tear samples are punched out using a die, making a rectangle 1.5 inches by 1 inch by 1 inch with a specimen-centered notch ½ inch long, sliced perpendicular to the longest dimension. The specimen is gripped equal distance from the notch and pulled by the Instron. Shear strain and stress is recorded and the area under the stress-strain curve from strain zero to the final failure is measured. This area is the total tear energy. The results in Table 5 indicate that an increase in constrained tear strength is imparted by the discrete carbon nanotubes combined with the plasticizer.

TABLE 4

| Ingredient | Control | 2 phr dCNT | 3 phr dCNT |
|---|---|---|---|
| Nitrile Rubber (Nipol 3640S) | 100 | 100 | 100 |
| 20% dCNT in TOTM | 0 | 10 | 15 |
| N774 Carbon Black | 80 | 75 | 75 |
| Polyester sebacate plasticizer (Paraplex G-25) | 15 | 7 | 3 |
| Coumarone Indene Resin (Cumar P25) | 10 | 10 | 10 |
| Stearic Acid | 1 | 1 | 1 |
| Zinc Oxide (Kadox 911) | 5 | 5 | 5 |
| Antioxidant (Vanox CDPA) | 2 | 2 | 2 |
| Antioxidant (Santoflex 6PPD) | 2 | 2 | 2 |
| High molecular fatty acid esters (Struktol WB212) | 2 | 2 | 2 |
| Accelerator DTDM | 2 | 2 | 2 |
| Accelerator (Morfax) | 2.26 | 2.26 | 2.26 |
| Accelerator TMTM | 1 | 1 | 1 |

TABLE 5

| Description | Constrained Tear (psi) |
|---|---|
| Control | 482 |
| 2 phr dCNT | 537 |
| 3 phr dCNT | 574 |

Example 7

The discrete carbon nanotubes and plasticizer composition of Example 5 comprising 20% discrete carbon nanotubes and 80% TOTM (trioctyle trimellitate) is added at concentrations 3 parts per hundred resin (phr) of discrete carbon nanotubes to a nitrile rubber formulation (Table 6). The oil concentration of the compound is adjusted to compensate for the additional oil from the composition of this invention so that all formulations have equivalent oil concentrations. A comparative compound is prepared with carbon nanotubes as received (Flotube C9000, CNano) (Table 6). Carbon black content is adjusted so that the measured hardness is the same for the three samples. The Shore A hardness is 67 for the control and 67 for the 3 phr CNT of this invention and 68 for the 3 phr "As is" carbon nanotubes (C9000). The constrained tear is measured as described in Example 6. The discrete carbon nanotubes and oil composition (dCNT) of this invention have higher total tear energy than the entangled carbon nanotubes (C9000) and the control. The tear energy of entangled carbon nanotubes, C9000, is worse than the control. (Table 7).

TABLE 6

| Ingredient | Control | 3 phr dCNT | 3 phr C9000 |
| --- | --- | --- | --- |
| Nitrile Rubber (Nipol 3640S) | 100 | 100 | 100 |
| 20% dCNT in TOTM | 0 | 15 | 0 |
| MWCNT as received (C9000, CNano) | 0 | 0 | 3 |
| N774 Carbon Black | 80 | 75 | 75 |
| Polyester sebacate plasticizer (Paraplex G-25) | 15 | 3 | 15 |
| Coumarone Indene Resin (Cumar P25) | 10 | 10 | 10 |
| Stearic Acid | 1 | 1 | 1 |
| Zinc Oxide (Kadox 911) | 5 | 5 | 5 |
| Antioxidant (Vanox CDPA) | 2 | 2 | 2 |
| Antioxidant (Santoflex 6PPD) | 2 | 2 | 2 |
| High molecular fatty acid esters (Struktol WB212) | 2 | 2 | 2 |
| Accelerator DTDM | 2 | 2 | 2 |
| Accelerator (Morfax) | 2.26 | 2.26 | 2.26 |
| Accelerator TMTM | 1 | 1 | 1 |

TABLE 7

| Description | Constrained Tear (psi) |
| --- | --- |
| Control | 482 |
| 3 phr dCNT | 574 |
| 3 phr C9000 | 394 |

It is known to those practiced in the art that the addition of filler to a rubber compound will increase the viscosity of the compound. Unexpectedly, the addition of discrete carbon nanotube and oil mixture from Example 7 did not increase the viscosity but instead decreased viscosity, while the entangled carbon nanotubes of Example 7 (C9000) increased the viscosity. The viscosity is measured using a Mooney Rheometer at 125° C. The initial viscosity measured is descriptive of the processability of the compound. The viscosity of the compound containing the discrete carbon nanotubes of this invention and described in Example 7 is found to be equal to the control while the compound containing the entangled carbon nanotubes (C9000) is found to be higher than the control (Table 8).

TABLE 8

| Description | Minimum Mooney Viscosity ML(1 + 30) |
| --- | --- |
| Control | 23.1 |
| 3 phr dCNT | 23.1 |
| 3 phr C9000 | 26.6 |

Example 8

A calibration curve for the UV absorption of niacin as a function of the concentration of niacin in water is determined. A solution is prepared by mixing 0.0578 grams of discrete functionalized carbon nanotubes of this invention with 0.0134 grams of niacin in 25 ml of water [0.231 grams niacin/gram of carbon nanotube]. The tubes are allowed to settle and an aliquot of the fluid above the tubes is removed hourly. The UV-vis absorption of this aliquot is measured and the resulting amount of niacin in the solution is recorded. The amount of niacin in solution stabilizes after 6 hours. A final sample is taken 20 hours after mixing. The difference between the amounts of niacin remaining in the solution and the original amount is determined to be the amount of niacin associated with the discrete functionalized carbon nanotubes. It is found that 0.0746 grams of niacin associated with each gram of carbon nanotubes. The total amount of niacin absorbed by the carbon nanotubes is 0.0043 grams. Given an average carbon nanotube length of 1000 nm, external diameter of 12 nm and internal diameter of 5 nm, the available volume within the tube is 0.093 $cm^3$ per gram of carbon nanotubes. Since the density of niacin is 1.473 $g/cm^3$, then the maximum amount of niacin that can fit in the tubes is 0.137 grams. Therefore, the measured absorption of 0.0746 g niacin/g CNT amount could be confined to the interior of the tube.

Example 9

A poly (vinyl alcohol), PVOH, is sufficiently large (30 kDa-70 kDa) that it cannot be absorbed internally in a carbon nanotube. PVOH is used as a surfactant for carbon nanotubes because it associates and wraps the exterior of the carbon nanotube. In this experiment, PVOH is added to a mixture of 0.0535 g of carbon nanotubes and 0.0139 g niacin (0.26 grams niacin to 1 gram carbon nanotubes) in 25 ml water. This is allowed to rest overnight. Using the UV-vis technique of Example 1, the amount of niacin associated with the carbon nanotubes is determined to be 0.0561 grams niacin per gram of carbon nanotubes, less than the 0.0746 grams in example 1. The total amount of niacin absorbed is 0.003 grams.

Calculations are made using carbon nanotube length of 1000 nm, external diameter of 12 nm and internal diameter of 5 nm. Given the density of PVOH is 1.1 $g/cm^3$ and the ratio of PVOH to carbon nanotubes was 0.23 to 1, the average layer thickness of PVOH on the carbon nanotube is 0.6 nm. Therefore there is sufficient PVOH to encapsulate the carbon nanotube and displace any niacin on the surface of the tube and the measured amount of 0.0561 grams of niacin per gram of carbon nanotubes is in the interior of the carbon nanotube.

In another example the discrete functionalized carbon nanotubes can be dispersed in a polymeric matrix, for example polyethylene oxide, in the melt or in a solution and the payload molecule added.

A small sample of the filter cake is dried in vacuum at 100° C. for 4 hours and a thermogravimetric analysis performed at 10° C./min heating rate in nitrogen from 100° C. to 600° C. The amount of oxidized species on the fiber is taken as the weight loss between 200 and 600° C. The dispersion of individual tubes (discrete) is also determined by UV spectroscopy. Water is added to the wet cake to give a 0.5% weight carbon nanotube suspension, then sodium dodecylbenzene sulfonic acid is added at a concentration of 1.5 times the mass of oxidized carbon nanotubes. The solution is sonicated for 30 minutes using a sonicator bath then diluted to a concentration of $2.5 \times 10^{-5}$ g carbon nanotubes/ml. The carbon nanotubes will give a UV absorption at 500 nm of at least 1.2 absorption units.

The improvement in flow processibility of the compositions can be determined using a rheometer, for example, utilizing concentric cylinders with a well-defined geometry to measure a fluid's resistance to flow and determine its viscous behavior. While relative rotation of the outer cylinder causes the composition to flow, its resistance to deformation imposes a shear stress on the inner wall of the cup, measured in units of Pa.

TABLE 9

Lengths (nm)

| | Condition 1 | Condition 2 | Condition 3 |
|---|---|---|---|
| Mean | 424 | 487 | 721 |
| Standard Error | 25.3 | 34.9 | 50 |
| Median | 407 | 417.0 | 672 |
| Standard Deviation | 177 | 281 | 315 |
| Sample Variance | 31461 | 79108 | 99418 |
| Kurtosis | −0.83 | 1.5 | −0.02 |
| Skewness | 0.03 | 1.2 | 0.64 |
| Range | 650 | 1270.0 | 1364 |
| Minimum | 85 | 85.0 | 161 |
| Maximum | 735 | 1355 | 1525 |

Condition 1 is an example of a narrow distribution with low mean length.
Condition 2 is an example of broad distribution with low mean length.
Condition 3 is an example of high mean length and broad distribution.

To determine tube lengths, a sample of tubes is diluted in isopropyl alcohol and sonicated for 30 minutes. It is then deposited onto a silica wafer and images are taken at 15 kV and 20,000× magnification by SEM. Three images are taken at different locations. Utilizing the JEOL software (included with the SEM) a minimum of 2 lines are drawn across on each image and measure the length of tubes that intersect this line.

Skewness is a measure of the asymmetry of a probability distribution. A positive value means the tail on the right side of the distribution histogram is longer than the left side and vice versa. Positive skewness is preferred which indicates means more tubes of long lengths. A value of zero means a relatively even distribution on both sides of the mean value.

Kurtosis is the measure of the shape of the distribution curve and is generally relative to a normal distribution. Both skewness and kurtosis are unitless. The following table shows representative values of discrete carbon nanotubes diameters:

TABLE 10

| Diameter (unrelated to condition above) | | | |
|---|---|---|---|
| Mean diameter (nm*) | | 12.5 | |
| Median diameter (nm) | | 11.5 | |
| Kurtosis | 3.6 | | |
| Skewness | 1.8 | | |
| Calculated aspect ratio (L/D) | 34 | 39 | 58 |

*nm = nanometer

Example 10

A solution of discrete multi-wall carbon nanotubes made according to Example 3 herein and water (at a discrete carbon nanotube concentration of between 0.5 wt % and 5 wt %) is sonicated to ensure even dispersion of tubes. To this solution, enough pectinase (produced from *Aspergillus aculaceatus*, Sigma-Aldrich) to affect a net concentration of between 2 wt % and 15 wt % pectinase relative to the weight of MR, is added, while stirring. A solution simulating hydraulic fracturing fluid, where the key component is a concentration of hydroxypropyl guar (Tiguar HP 8 FF, Solvay) at 5000 ppm that has been cross-linked with sodium borate, is produced using normal industry techniques. The enzyme-loaded carbon nanotubes are added to this borate-crosslinked guar solution to such an extent that the final net pectinase concentration in the entire mixture is between 0.01 wt % and 0.5 wt % pectinase. This mixture is immediately placed into a Brookfield RST Rheometer and changes in viscosity as a function of time are taken to indicate the degradation of the cross-linked hydroxypropyl guar polymer system and the test is concluded when the viscosity approaches an asymptotic limit. The untreated cross-linked hydroxypropyl guar system's viscosity is also measured using a Brookfield RST Rheometer and is compared to the enzyme-loaded carbon nanotube guar system's viscosity. The enzyme-carbon-nanotube treated guar system is found to have a decreased viscosity of at least 10% when compared to the untreated cross-linked hydroxypropyl guar system.

Example 11

A solution of discrete multi-wall carbon nanotubes made according to Example 3 herein and water (at a discrete carbon nanotube concentration of between 0.5 wt % and 5 wt %) is sonicated to ensure even dispersion of tubes. To this solution, enough magnesium peroxide (produced by Sigma-Aldrich) to affect a net concentration of between 2 wt % and 15 wt % magnesium peroxide relative to the weight of MR, is added, while stirring. A solution simulating hydraulic fracturing fluid, where the key component is a concentration of hydroxypropyl guar (Tiguar HP 8 FF, Solvay) at 5000 ppm that has been cross-linked with sodium borate, is produced using normal industry techniques. The magnesium peroxide—loaded carbon nanotubes are added to this borate-crosslinked guar solution to such an extent that the final net magnesium peroxide concentration in the entire mixture is between 0.01 wt % and 0.5 wt % magnesium peroxide. This mixture is immediately placed into a Brookfield RST Rheometer and changes in viscosity as a function of time are taken to indicate the degradation of the cross-linked hydroxypropyl guar polymer system and the test is concluded when the viscosity approaches an asymptotic limit. The untreated cross-linked hydroxypropyl guar system's viscosity is also measured using a Brookfield RST Rheometer and is compared to the magnesium peroxide-loaded carbon nanotube guar system's viscosity. The magnesium peroxide-carbon-nanotube treated guar system is found to have a decreased viscosity of at least 10% when compared to the untreated cross-linked hydroxypropyl guar system.

The disclosed embodiments and aspects of embodiments may relate to the following:

One embodiment of the present invention is a composition useful for treating hydraulic fracturing fluids, preferably at least one aqueous fluid, comprising a plurality of discrete carbon nanotubes, preferably discrete multi-wall carbon nanotubes, wherein the discrete carbon nanotubes comprise an interior and exterior surface, each surface comprising an interior surface oxidized species content and an exterior surface oxidized species content, and at least one degradative molecule that is attached on the interior or exterior surface of the plurality of discrete carbon nanotubes. Preferably, the degradative molecule is at least one enzyme, especially wherein the enzyme is attached via Van der Waals, ionic, or covalent bonding. The degradative molecule can be at least one oxidizer, preferably wherein the oxidizer is attached via Van de Waals, ionic, or covalent bonding. Preferably, the oxidizer is selected from the group consisting of peroxides, chlorides, sulfates, and persulfates.

The discrete multi-wall carbon nanotubes used in the invention preferably comprise a plurality of open ended tubes.

Preferably, the oxidized species comprising the discrete carbon nanotubes is selected from the group consisting of carboxylic acids, phenols, aldehydes, ketones, hydroxyl, carboxylic, ether linkages, and combinations thereof.

The enzyme is preferably selected from the group consisting of hemicellulases, encapsulated enzyme breakers, GBW-12CD, LEB-H, gammanase, endo-mannanase, β-mannanase, pectinase, and Econo Gelbreak-EL2X, and mixtures thereof.

The degradative molecule can comprise one or more types of enzyme, wherein the enzyme types are selected from the group consisting of oxidoreductases, transferases, hydrolases, lyases, isomerases, and ligases.

The degradative molecule is typically present at a concentration of 0.1 wt % to 20 wt %, preferably 2 wt % to 15 wt %.

The compositions of the invention can further comprise at least one surfactant, preferably at least one organic surfactant. The compositions of the invention can also further comprise at least one polymer, preferably at least one organic polymer. The polymer can be at least partially crosslinked. Preferably, the organic polymers are selected from the group consisting of guar, hydroxyalkylguar, carboxyalkylhydroxyguar, carboxyalkylhydroxyalkylguar, cellulose, hydroxyalkylcellulose, carboxyalkyl-hydroxyalkyl-cellulose, polyacrylamide, polyethylene oxide, xanthum, and mixtures thereof. The surfactant is preferably selected from the group consisting of anionic, ionic, non-ionic, gemini, and zwitterionic surfactants, and mixtures thereof.

The compositions of the invention can have a viscosity less than an identical composition comprising the same elements, except the carbon nanotubes are not discrete but are entangled as-manufactured. The compositions of the invention can also have a viscosity less than a comparable composition which is made with non-discrete, entangled carbon nanotubes as opposed to discrete carbon nanotubes.

Another aspect of the invention is a composition useful for treating aqueous fluids comprising a plurality of discrete carbon nanotubes, wherein the discrete carbon nanotubes comprise an interior and exterior surface, each surface comprising an interior surface oxidized species content and an exterior surface oxidized species content, and at least one biocide that is attached on the interior or exterior of the discrete carbon nanotubes. The biocide may be attached on the interior or exterior of the discrete carbon nanotube via Van der Waals, ionic or covalent bonding to the nanotube surfaces. Preferably, the biocide is selected from the group consisting of lytic biocides, cationic quaternary ammonium/amine compounds ("QACs" or "quats") didecyl dimethylammonium chloride (DDAC or decanaminium, alkyldimethylbenzylammonium chloride (ADBAC, benzalkonium chloride, BAC, BC, or benzenemethanaminium), dibromonitrilopropionamide, chlorine dioxide, tributyl tetradecyl phosphonim chloride, alkyl dimethyl benzyl phosphonim chloride, sodium hypchlorite, dazomet, dimethyloxazolidone, trimetyloxazolidine, N-bromosuccinimide, bronopol, peracetic acid, electrophilic biocides, glutaraldehyde, tetrakis(hydroxymethyl)phosphonium sulfate (THPS), chloromethylisothiazolinone (CMIT, or MCI, 5-chloro-2-methyl-3(2H)-isothiazolinone), methylisothiazolinone (MIT, or MI, 2-methyl-3(2H)-isothiazolinone), and mixtures thereof.

Other aspects of the invention include use of the inventive compositions comprising the degradative molecule as a targeting, sequestering and/or labeling agent in ground water remediation and/or as a targeting, sequestering and/or labeling agent in subterranean earth oil field drilling operations and/or ground water remediation in said drilling operations.

Other embodiments of the invention include a composition comprising a plurality of discrete carbon nanotubes, preferably discrete multi-wall carbon nanotubes, wherein the discrete carbon nanotubes comprise an interior and exterior surface, each surface comprising an interior surface oxidized species content and an exterior surface oxidized species content, preferably wherein the interior surface oxidized species content differs from the exterior surface oxidized species content by at least 20%, and as high as 100%, more preferably wherein the interior surface oxidized species content is less than the exterior surface oxidized species content. In alternative embodiments the interior surface oxidized species content is greater than the exterior surface oxidized species content.

The interior surface oxidized species content can be up to 6, preferably up to 3 weight percent relative to carbon nanotube weight, preferably from about 0.01 to about 3 weight percent relative to carbon nanotube weight, more preferably from about 0.01 to about 2, most preferably from about 0.01 to about 1. Especially preferred interior surface oxidized species content is from zero to about 0.01 weight percent relative to carbon nanotube weight. The exterior surface oxidized species content can be from about 1 to about 6 weight percent relative to carbon nanotube weight, preferably from about 1 to about 4, more preferably from about 1 to about 2 weight percent relative to carbon nanotube weight. The interior and exterior surface oxidized species content totals can be from about 1 to about 9 weight percent relative to carbon nanotube weight.

Another embodiment of the invention is a composition comprising a plurality of discrete carbon nanotubes, wherein the discrete carbon nanotubes comprise an interior and exterior surface, each surface comprising an interior surface and an exterior surface oxidized species content, wherein the interior surface oxidized species content comprises from about 0.01 to less than about 1 percent relative to carbon nanotube weight and the exterior surface oxidized species content comprises more than about 1 to about 3 percent relative to carbon nanotube weight. The discrete carbon nanotubes of the embodiments herein preferably comprise a plurality of open ended tubes, more preferably the plurality of discrete carbon nanotubes comprise a plurality of open ended tubes. The discrete carbon nanotubes of the embodiments herein are especially preferred wherein the inner and outer surface oxidation difference is at least about 0.2 weight percent.

The compositions described herein can be used as an ion transport. Various species or classes of compounds/drugs/chemicals which demonstrate this ion transport effect can be used, including ionic, some non-ionic compounds, hydrophobic or hydrophilic compounds. The new carbon nanotubes disclosed herein are also useful in ground water remediation wherein the nanotubes can carry chemicals inside the inner wall that can be released once the nanotubes are in the ground avoiding chemical loss due to absorbance by ground material until the chemicals are where they are needed. The compositions comprising the novel discrete targeted oxidized carbon nanotubes can also be used as a component in, or as, a sensor. The compositions disclosed herein can also be used as a component in, or as, drug delivery or controlled release formulations. The amount of oxidation inside the nanotubes affects the amount of the drug that can be loaded inside the carbon nanotube depending on the structure of the drug. The pH of the drug affects the amount of drug that can be loaded depending on the pH and the chemical structure of the drug and the inside of the nanotube. Batteries comprising the compositions disclosed herein are also useful. Such batteries include lithium, nickel cadmium, or lead acid types. Formulations comprising the compositions disclosed herein can further comprise an epoxy, a polyurethane, or an elastomer. Such formulations can be in the form of a dispersion. The formulations can also include nanoplate structures. The compositions can further comprise at least one hydrophobic material in contact with at least one interior surface.

The present application also relates to a composition comprising a plurality of discrete carbon nanotubes with and without a plasticizer wherein the discrete carbon nanotubes have an aspect ratio (ratio of length divided by diameter) of 10 to about 500, and wherein the carbon nanotubes are functionalized with oxygen species on their outermost wall surface. The discrete carbon nanotubes comprise an interior and exterior surface, each surface comprising an interior surface and exterior surface oxidized species content wherein the interior surface oxidized species content comprises from about 0.01 to less than about 1 percent relative to carbon nanotube weight and the exterior surface oxidized species content comprises more than about 1 to about 3 percent relative to carbon nanotube weight. The oxygen species can comprise carboxylic acids, hydroxyl, ketones, aldehydes and phenolics, or combinations thereof.

The composition can further comprise a plasticizer selected from the group consisting of dicarboxylic/tricarboxylic esters, timellitates, adipates, sebacates, maleates, glycols and polyethers, polymeric plasticizers, bio-based plasticizers, and mixtures thereof. The term "plasticizer" includes both synthetic and natural waxes, and mixtures thereof. An example of a natural wax is carnauba wax. An example of a synthetic wax (sometimes also called a degradative wax) is a very low molecular weight polyethylene polymer trademarked ENGAGE™ and made by The Dow Chemical Company. Very low molecular weight polyethylene waxes have a molecular weight from 300 to 10000, preferably 2000 to 4000. The compositions disclosed herein can comprise at least one of these waxes. The composition can comprise plasticizers comprising a process oil selected from the group consisting of naphthenic oils, paraffin oils, paraben oils, aromatic oils, vegetable oils, seed oils, and mixtures thereof. The composition can further comprise a plasticizer selected from the group of water immiscible solvents consisting of but not limited to zylene, pentane, methylethyle ketone, hexane, heptane, ethyl actetate, ethers, dicloromethane, dichloroethane, cyclohexane, chloroform, carbon tetrachloride, butyl acetate butanol, benzene or mixtures thereof. In yet another embodiment the composition further comprises an inorganic filler selected from the group consisting of silica, nano-clays, carbon black, graphene, glass fibers, and mixtures thereof. In another embodiment the composition is in the form of free flowing particles. In another embodiment, the composition comprises a plurality of discrete carbon nanotubes and a plasticizer wherein the discrete carbon nanotubes comprise from about 10 weight percent to about 90 weight percent, preferably 10 weight percent to 40 weight percent, most preferably 10 to 20 weight percent.

An another embodiment is a process to form a composition comprising discrete carbon nanotubes in a plasticizer comprising the steps of: a) selecting a plurality of discrete carbon nanotubes having an average aspect ratio of from about 10 to about 500, and an oxidative species content total level from about 1 to about 15% by weight, b) suspending the discrete carbon nanotubes in an aqueous medium (water) at a nanotube concentration from about 1% to about 10% by weight to form an aqueous medium/nanotube slurry, c) mixing the carbon nanotube/aqueous medium (e.g., water) slurry with at least one plasticizer at a temperature from about 30° C. to about 100° C. for sufficient time that the carbon nanotubes migrate from the water to the plasticizer to form a wet nanotube/plasticizer mixture, e) separating the water from the wet carbon nanotube/plasticizer mixture to form a dry nanotube/plasticizer mixture, and f) removing residual water from the dry nanotube/plasticizer mixture by drying from about 40° C. to about 120° C. to form an anhydrous nanotube/plasticizer mixture.

Another embodiment is the composition of discrete carbon nanotubes in a plasticizer further mixed with a least one rubber. The rubber can be natural or synthetic rubbers and is preferably selected from the group consisting of natural rubbers, polyisobutylene, polybutadiene and styrene-butadiene rubber, butyl rubber, polyisoprene, styrene-isoprene rubbers, styrene-isoprene rubbers, ethylene, propylene diene rubbers, silicones, polyurethanes, polyester-polyethers, hydrogenated and non-hydrogenated nitrile rubbers, halogen modified elastomers, fluoro-elastomers, and combinations thereof.

Another embodiment is the composition of discrete carbon nanotubes in a plasticizer further mixed with at least one thermoplastic polymer or at least one thermoplastic elastomer. The thermoplastic can be selected from but is not limited to acrylics, polyamides, polyethylenes, polystyrenes, polycarbonates, methacrylics, phenols, polypropylene, polyolefins, such as polyolefin plastomers and elastomers, EPDM, and copolymers of ethylene, propylene and functional monomers.

Yet another embodiment is the composition of discrete carbon nanotubes in a plasticizer further mixed with at least one thermoset polymer, preferably an epoxy, or a polyurethane. The thermoset polymers can be selected from but is not limited to epoxy, polyurethane, or unsaturated polyester resins.

Discrete carbon nanotubes having specific properties can also be used in payload or drug molecule delivery, especially for use in the human body. The open ended multi-wall discrete carbon nanotubes preferably comprise at least one end having attached thereto a bio-compatible polymer, amino acid, protein or peptide. The attachment may be covalently, ionically, hydrogen bonding or pi-pi bonding in nature. The functionalized discrete carbon nanotubes can include at least one tissue-targeting moiety. Use of tissue-targeting moieties is well known in the art to provide directed delivery of a drug to a particular tissue in vivo, such as a tumor tissue. The compositions may also be directed to certain cellular receptors, such as through receptor ligands attached to the functionalized carbon nanotube. In some disease states, such as but not limited to cancer, certain cellular receptors are either overexpressed or in a high-activity binding state. Direction of the compositions herein to cellular receptors advantageously provides a means of targeting a particular tissue. The at least one tissue-targeting moiety is selected from a group including, but not limited to, aptamers, nucleic acids, antibodies, antibody fragments, saccharides, peptides, proteins, hormones, receptor ligands, and synthetic derivatives thereof. Various cellular recognition sites exist for these moieties, allowing for directed tissue targeting of the compositions.

The payload molecule can be selected from the group consisting of a drug molecule, a radiotracer molecule, a radiotherapy molecule, diagnostic imaging molecule, fluorescent tracer molecule, a protein molecule, and combinations thereof. Exemplary types of payload molecules that may be covalently or non-covalently associated with the discrete functionalized carbon nanotubes disclosed herein may include, but are not limited to, proton pump inhibitors, H2-receptor antagonists, cytoprotectants, prostaglandin analogues, beta blockers, calcium channel blockers, diuretics, cardiac glycosides, antiarrhythmics, antianginals, vasoconstrictors, vasodilators, ACE inhibitors, angiotensin receptor blockers, alpha blockers, anticoagulants, antiplatelet drugs, fibrinolytics, hypolipidemic agents, statins, hypnotics, antipsychotics, antidepressants, monoamine oxidase inhibitors, selective serotonin reuptake inhibitors, antiemetics, anticonvulsants, anxiolytic, barbiturates, stimulants, amphetamines, benzodiazepines, dopamine antagonists, antihistamines, cholinergics, anticholinergics, emetics, cannabinoids, 5-HT antagonists, NSAIDs, opioids, bronchodilator, antiallergics, mucolytics, corticosteroids, beta-receptor antagonists, anticholinergics, steroids, androgens, antiandrogens, growth hormones, thyroid hormones, anti-thyroid drugs, vasopressin analogues, antibiotics, antifungals, antituberculous drugs, antimalarials, antiviral drugs, antiprotozoal drugs, radioprotectants, chemotherapy drugs, cytostatic drugs, and cytotoxic drugs Another aspect of the invention is in a transdermal patch composition comprising discrete carbon nanotubes described herein. Another aspect of the invention is in a bone repair composition comprising discrete carbon nanotubes described herein.

EMBODIMENTS

Specific Embodiments Disclosed Include:
1. A composition useful for treating hydraulic fracturing fluids comprising a plurality of discrete carbon nanotubes, wherein the discrete carbon nanotubes comprise an interior and exterior surface, each surface comprising an interior surface oxidized species content and an exterior surface oxidized species content, and at least one degradative molecule that is attached on the interior or exterior surface of the plurality of discrete carbon nanotubes.
2. The composition of Embodiment 1, wherein the fluid is aqueous.
3. The composition of Embodiment 1, wherein the degradative molecule is at least one enzyme.
4. The composition of Embodiment 3, wherein the enzyme is attached via Van der Waals, ionic, or covalent bonding.
5. The composition of Embodiment 1, wherein the degradative molecule is an oxidizer.
6. The composition of Embodiment 5, wherein the oxidizer is attached via Van de Waals, ionic, or covalent bonding.
7. The composition of Embodiment 3, wherein the enzyme is selected from the group consisting of hemicellulases, encapsulated enzyme breakers, GBW-12CD, LEB-H, gammanase, endo-mannanase, β-mannanase, pectinase, and Econo Gelbreak-EL2X, and mixtures thereof.
8. The composition of Embodiment 1, wherein the degradative molecule comprises one or more types of enzyme, wherein the enzyme types are selected from the group consisting of oxidoreductases, transferases, hydrolases, lyases, isomerases, and ligases.
9. The composition of Embodiment 1, wherein the degradative molecule is an oxidizer selected from the group consisting of peroxides, chlorides, sulfates, and persulfates.
10. The composition of Embodiment 1, wherein the degradative molecule is present at a concentration of 0.1 wt % to 20 wt %, preferably 2 wt % to 15 wt %.
11. The composition of Embodiment 1, wherein the composition further comprises at least one surfactant, preferably at least one organic surfactant.
12. The composition of Embodiment 1, wherein the composition further comprises at least one polymer, preferably at least one organic polymer.
13. The composition of Embodiment 12, wherein the polymer is at least partially crosslinked.
14. The composition of Embodiment 10, wherein the surfactant is selected from the group consisting of anionic, ionic, non-ionic, gemini, and zwitterionic surfactants, and mixtures thereof.
15. The composition of Embodiment 12 having a viscosity less than an identical composition comprising the same elements, except the carbon nanotubes are not discrete but are entangled as-manufactured.
16. The composition of Embodiment 12, wherein the organic polymers are selected from the group consisting of guar, hydroxyalkylguar, carboxyalkylhydroxyguar, carboxyalkylhydroxyalkylguar, cellulose, hydroxyalkylcellulose, carboxyalkyl-hydroxyalkylcellulose, polyacrylamide, polyethylene oxide, xanthum, and mixtures thereof.
17. A composition useful for treating aqueous fluids comprising a plurality of discrete carbon nanotubes, wherein the discrete carbon nanotubes comprise an interior and exterior surface, each surface comprising an interior surface oxidized species content and an exterior surface oxidized species content, and at least one biocide that is attached on the interior or exterior of the discrete carbon nanotubes.
18. The composition of Embodiment 17, wherein the biocide is attached via Van der Waals, ionic or covalent bonding.
19. The composition of Embodiment 17, wherein the biocide is selected from the group consisting of lytic biocides, cationic quaternary ammonium/amine compounds ("QACs" or "quats") didecyl dimethylammonium chloride (DDAC or decanaminium, alkyldimethylbenzylammonium chloride (ADBAC, benzalkonium chloride, BAC, BC, or benzenemethanaminium), dibromonitrilopropionamide, chlorine dioxide, tributyl tetradecyl phosphonim chloride, alkyl dimethyl benzyl phosphonim chloride, sodium hypchlorite, dazomet, dimethyloxazolidone, trimetyloxazolidine, N-bromosuccinimide, bronopol, peracetic acid, electrophilic biocides, glutaraldehyde, tetrakis(hydroxymethyl) phosphonium sulfate (THPS), chloromethylisothiazolinone (CMIT, or MCI, 5-chloro-2-methyl-3(2H)-isothiazolinone), methylisothiazolinone (MIT, or MI, 2-methyl-3(2H)-isothiazolinone), and mixtures thereof.

20. The composition of Embodiment 1, wherein the interior surface oxidized species content differs from the exterior surface oxidized species content by at least 20%, and as high as 100%.
21. The composition of Embodiment 1 wherein the interior surface oxidized species content is less than the exterior surface oxidized species content.
22. The composition of Embodiment 1 wherein the interior surface oxidized species content is greater than the exterior surface oxidized species content.
23. The composition of Embodiment 1 wherein the interior surface oxidized species content is at least 99% greater than the exterior surface oxidized species content.
24. The composition of Embodiment 1 wherein the exterior surface oxidized species content is at least 99% greater than the interior surface oxidized species content.
25. The composition of Embodiment 1 wherein the interior and exterior surface oxidized species content totals from about 1 to about 9 weight percent based on carbon nanotube weight.
26. The composition of Embodiment 1 wherein the discrete carbon nanotubes comprise a plurality of open ended tubes.
27. The composition of Embodiment 1, wherein the discrete carbon nanotubes are multiwalled carbon nanotubes.
28. The composition of Embodiment 1 wherein the oxidized species is selected from the group consisting of carboxylic acids, phenols, aldehydes, ketones, hydroxyl, carboxylic, ether linkages, and combinations thereof.
29. The composition of Embodiment 1 wherein the total oxidized species content of the interior surface and exterior surface comprises from about 1% to 15% by weight of the carbon nanotubes.
30. The composition of Embodiment 17, wherein the interior surface oxidized species content differs from the exterior surface oxidized species content by at least 20%, and as high as 100%.
31. The composition of Embodiment 17, wherein the interior surface oxidized species content is less than the exterior surface oxidized species content.
32. The composition of Embodiment 17, wherein the interior surface oxidized species content is greater than the exterior surface oxidized species content.
33. The composition of Embodiment 17, wherein the interior surface oxidized species content is at least 99% greater than the exterior surface oxidized species content.
34. The composition of Embodiment 17, wherein the exterior surface oxidized species content is at least 99% greater than the interior surface oxidized species content.
35. The composition of Embodiment 17, wherein the interior and exterior surface oxidized species content totals from about 1 to about 9 weight percent based on carbon nanotube weight.
36. The composition of Embodiment 17, wherein the discrete carbon nanotubes comprise a plurality of open ended tubes.
37. The composition of Embodiment 17, wherein the discrete carbon nanotubes are multiwalled carbon nanotubes.
38. The composition of Embodiment 17, wherein the oxidized species is selected from the group consisting of carboxylic acids, phenols, aldehydes, ketones, hydroxyl, carboxylic, ether linkages, and combinations thereof.
39. The composition of Embodiment 17, wherein the total oxidized species content of the interior surface and exterior surface comprises from about 1% to 15% by weight of the carbon nanotubes.
40. The composition of Embodiment 1, wherein the interior surface oxidized species content differs from the exterior surface oxidized species content by at least 20%, and as high as 100%.
41. The composition of Embodiment 17, wherein the interior surface oxidized species content is less than the exterior surface oxidized species content.
42. The composition of Embodiment 17, wherein the interior surface oxidized species content is greater than the exterior surface oxidized species content.
43. The composition of Embodiment 17, wherein the interior surface oxidized species content is at least 99% greater than the exterior surface oxidized species content.
44. The composition of Embodiment 17, wherein the exterior surface oxidized species content is at least 99% greater than the interior surface oxidized species content.
45. The composition of Embodiment 17, wherein the interior and exterior surface oxidized species content totals from about 1 to about 9 weight percent based on carbon nanotube weight.
46. The composition of Embodiment 17, wherein the discrete carbon nanotubes comprise a plurality of open ended tubes.
47. The composition of Embodiment 17, wherein the discrete carbon nanotubes are multiwalled carbon nanotubes.
48. The composition of Embodiment 17, wherein the oxidized species is selected from the group consisting of carboxylic acids, phenols, aldehydes, ketones, hydroxyl, carboxylic, ether linkages, and combinations thereof.
49. The composition of Embodiment 17, wherein the total oxidized species content of the interior surface and exterior surface comprises from about 1% to 15% by weight of the carbon nanotubes.
50. Use of the composition of Embodiment 1 as a targeting, sequestering and/or labeling agent in ground water remediation.
51. Use of the composition of Embodiment 1 as a targeting, sequestering and/or labeling agent in subterranean earth oil field drilling operations and/or ground water remediation in said drilling operations.
52. The compositions of Embodiment 12 wherein the viscosity is less than a comparable composition which is made with non-discrete, entangled carbon nanotubes instead of discrete carbon nanotubes.

The above description is for the purpose of teaching the person of ordinary skill in the art how to practice the present application, and it is not intended to detail all those obvious modifications and variations of it which will become apparent to the skilled worker upon reading the description. It is intended, however, that all such obvious modifications and variations be included within the scope of the present application, which is defined by the following claims. The claims are intended to cover the claimed components and steps in any sequence which is effective to meet the objectives there intended, unless the context specifically indicates the contrary.

The invention claimed is:

1. A composition comprising a plurality of discrete carbon nanotubes, wherein the discrete carbon nanotubes comprise an interior and exterior surface, the interior surface comprising an interior surface oxidized species content and the exterior surface comprising an exterior surface oxidized species content, wherein the interior surface oxidized species content is less than about 0.5 weight percent relative to carbon nanotube weight, and wherein the interior surface oxidized species content differs from the exterior surface oxidized species content by greater than 85%; wherein the composition further comprises a rubber.

2. The composition of claim 1 further comprising a plasticizer.

3. The composition of claim 1 wherein the plurality of discrete carbon nanotubes comprise an interior surface oxidized species content of from 0 to about 0.01 weight percent.

4. The composition of claim 1 wherein the interior and exterior surface oxidized species content totals from about 1 to about 9 weight percent based on carbon nanotube weight.

5. The composition of claim 1 wherein the plurality of discrete carbon nanotubes has a multimodal distribution of carbon nanotube length.

6. The composition of claim 1 wherein the plurality of discrete carbon nanotubes has a multimodal distribution of length to diameter ratio.

7. The composition of claim 1 wherein the interior surface oxidized species content differs from the exterior surface oxidized species content by greater than 99%.

8. The composition of claim 1 wherein the interior surface oxidized species content differs from the exterior surface oxidized species content by 100% or greater.

* * * * *